(12) United States Patent
Walker

(10) Patent No.: US 11,185,399 B2
(45) Date of Patent: Nov. 30, 2021

(54) FLEXIBLE SURGICAL SUCTION DEVICE AND METHOD

(71) Applicant: Anthony Walker, Carlsbad, CA (US)

(72) Inventor: Anthony Walker, Carlsbad, CA (US)

(73) Assignee: Nuflow Inc., Carlsbad, CA (US)

( * ) Notice: Subject to any disclaimer, the term of this patent is extended or adjusted under 35 U.S.C. 154(b) by 459 days.

(21) Appl. No.: 15/812,948

(22) Filed: Nov. 14, 2017

(65) Prior Publication Data

US 2019/0142558 A1    May 16, 2019

Related U.S. Application Data

(63) Continuation of application No. 13/366,641, filed on Feb. 6, 2012, now abandoned.

(51) Int. Cl.
| | |
|---|---|
| *A61C 17/08* | (2006.01) |
| *A61C 1/00* | (2006.01) |
| *A61L 15/24* | (2006.01) |
| *A61L 15/42* | (2006.01) |
| *A61F 13/36* | (2006.01) |
| *A61C 17/06* | (2006.01) |

(52) U.S. Cl.
CPC ............ *A61C 17/08* (2019.05); *A61C 1/0007* (2013.01); *A61F 13/36* (2013.01); *A61L 15/24* (2013.01); *A61L 15/425* (2013.01); *A61C 17/092* (2019.05); *A61C 17/096* (2019.05)

(58) Field of Classification Search
CPC ..... A61C 17/08; A61C 17/096; A61C 17/092; A61C 1/0007; A61B 17/24; A61F 13/36; A61L 15/24; A61L 15/425

USPC ......... 433/91–96; 601/162; 604/19; 606/196
See application file for complete search history.

(56) References Cited

U.S. PATENT DOCUMENTS

| | | |
|---|---|---|
| 587,358 A | 8/1897 | Anderson |
| 2,644,234 A * | 7/1953 | Scott ...................... A61C 17/08 433/94 |
| 2,672,143 A | 3/1954 | Gold et al. |
| | (Continued) | |

OTHER PUBLICATIONS

International Search Report and Written Opinion issued in Application No. PCT/US2013/024901, dated Feb. 26, 2013.
(Continued)

*Primary Examiner* — Yogesh P Patel
(74) *Attorney, Agent, or Firm* — Norton Rose Fulbright US LLP

(57) ABSTRACT

A siphoning device suited for automatically removing fluid/blood from a surgical site is described, having a length of sterile flexible tubing that is configurable into a loop, the tubing having a first open end, a second open end, and a central portion. A plurality of holes punctuate the circumference of either the first open end or the central portion of the loop, the one or more sets of holes being distributed along a longitudinal direction of the tubing. A sterile absorbent covering encompasses the one or more sets of the plurality of holes, the covering being permeable to bodily fluids. The siphoning device is connected to a vacuum system that generates a negative pressure, causing fluids that have accumulated in the absorbent covering to be withdrawn into the vacuum system. Accordingly, a durable, simple non-gauze system for automatically clearing blood/fluid from a surgical site is described.

8 Claims, 6 Drawing Sheets

(56) References Cited

U.S. PATENT DOCUMENTS

| | | | |
|---|---|---|---|
| 2,791,030 A * | 5/1957 | Tofflemire | A61C 17/08 433/39 |
| 2,873,528 A | 2/1959 | Thompson | |
| RE24,693 E | 9/1959 | Thompson | |
| 3,049,806 A | 8/1962 | Cofresi | |
| 3,225,444 A * | 12/1965 | Greenman | A61C 17/08 433/94 |
| RE26,470 E | 10/1968 | Deuschle et al. | |
| 3,426,430 A | 2/1969 | Newman | |
| 3,566,869 A | 3/1971 | Crowson | |
| 4,053,984 A | 10/1977 | Moss | |
| 4,233,025 A | 11/1980 | Larson et al. | |
| 4,260,378 A | 4/1981 | O'Neil | |
| 4,417,874 A | 11/1983 | Andersson et al. | |
| 4,511,329 A | 4/1985 | Diamond | |
| 4,576,817 A * | 3/1986 | Montgomery | A61L 15/38 424/616 |
| 4,773,898 A | 9/1988 | Begouen | |
| 4,778,111 A | 10/1988 | Leap | |
| 4,925,452 A | 5/1990 | Melinyshyn et al. | |
| 5,015,243 A | 5/1991 | Schifano | |
| 5,071,347 A | 12/1991 | McGuire | |
| 5,094,616 A | 3/1992 | Levenson | |
| 5,203,699 A * | 4/1993 | McGuire | A61C 17/08 433/93 |
| 5,215,539 A | 6/1993 | Schoolman | |
| 5,279,599 A | 1/1994 | Wilk | |
| 5,322,521 A | 6/1994 | Wilk | |
| 5,380,278 A | 1/1995 | Mombrinie | |
| 5,599,304 A | 2/1997 | Shaari | |
| 5,725,374 A | 3/1998 | Young | |
| 5,941,873 A | 8/1999 | Korenfeld | |
| 6,309,218 B1 | 10/2001 | Ellenbecker | |
| 7,141,047 B2 | 11/2006 | John | |
| 7,175,594 B2 | 2/2007 | Foulkes | |
| 7,261,560 B2 | 8/2007 | Abo | |
| 7,300,401 B2 | 11/2007 | Patrickus | |
| 7,488,315 B2 | 2/2009 | Falahee | |
| 8,074,656 B2 | 12/2011 | Vaska et al. | |
| 8,083,751 B2 | 12/2011 | Olsen et al. | |
| 2003/0186189 A1 | 10/2003 | Ito et al. | |
| 2004/0194787 A1 | 10/2004 | Miller | |
| 2005/0227199 A1 | 10/2005 | Patrickus | |
| 2006/0008764 A1 | 1/2006 | Abo | |
| 2009/0120447 A1 | 5/2009 | Vaska et al. | |
| 2009/0123886 A1 * | 5/2009 | Vaska | A61F 5/566 433/27 |
| 2009/0274991 A1 | 11/2009 | Black et al. | |
| 2010/0100181 A1 | 4/2010 | Makower et al. | |
| 2010/0179516 A1 | 7/2010 | Bengtson et al. | |
| 2011/0207076 A1 | 8/2011 | Hirsch et al. | |
| 2012/0017917 A1 | 1/2012 | Podmore et al. | |
| 2012/0199135 A1 | 8/2012 | Podmore et al. | |
| 2012/0237893 A1 | 9/2012 | Bergheim et al. | |
| 2012/0237894 A1 * | 9/2012 | Maycher | A61C 17/08 433/95 |

OTHER PUBLICATIONS

International Preliminary Report on Patentability issued in Application No. PCT/US2013/024901, dated Aug. 12, 2014.

\* cited by examiner

PRIOR ART

FLEXIBLE SURGICAL SUCTION DEVICE AND METHOD

CLAIM OF PRIORITY

This application is a continuation of U.S. patent application Ser. No. 13/366,641, filed Feb. 6, 2012, and incorporated herein in its entirety.

FIELD

This invention relates to surgical devices. More particularly, the invention relates to a flexible vacuum-assisted device suited for removing fluid and or blood from a surgical site.

BACKGROUND

Major surgery typically involves the cutting of tissue, causing a significant amount of blood to be released from the incisioned area. Conventional approaches to evacuating the released blood around the incisioned area is through the use of absorbent gauzes or sponges individually placed around the incisioned area, which then must be periodically replaced, as the gauzes/sponges become saturated. The released blood must be quickly removed as its accumulation and resulting coagulation obscures the operated area. Consequently, the process of placement, removal and replacement of the gauzes is an often-repeated procedure, resulting in the surgery taking longer; and, in some cases, the gauzes/sponges being errantly left inside the person after the surgery is complete. In the long history of surgery, there has not been any other approach to removing surgery-related blood and/or fluids.

Therefore, there has been a long-standing need in the surgical community for systems and methods that address these and other shortcomings in the medical field. Aspects of various systems and methods to address these issues are presented in the following detailed description.

SUMMARY

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In one aspect of the present disclosure, there is described a siphoning device suited for automatically removing fluid/blood from a surgical site, comprising: a length of sterile flexible tubing configurable into a loop, the tubing having a first open end, a second open end, and a central portion; at least one or more sets of a plurality of holes punctuating a circumference of either the first open end or the central portion of the loop, the one or more sets of holes being distributed along a longitudinal direction of the tubing; and a sterile absorbent covering encompassing the one or more sets of the plurality of holes, the covering being permeable to bodily fluids.

In another aspect of the present disclosure, there is described a siphoning device suited for automatically removing fluid/blood from a surgical site, comprising: a plurality of sterile flexible tubings having first open ends and second open ends; at least one or more sets of a plurality of holes punctuating a circumference of the first open ends, the one or more sets of holes being distributed along a longitudinal direction of the plurality of tubings; and a sterile absorbent covering encompassing the one or more sets of the plurality of holes, the covering being permeable to bodily fluids.

In yet another aspect of the present disclosure, there is described a method for automatically removing fluid blood from a surgical site, comprising: obtaining a fluid/blood siphoning device comprising: a length of sterile flexible tubing configurable into a loop, the tubing having a first open end, a second open end, and a central portion; at least one or more sets of a plurality of holes punctuating a circumference of either the first open end or the central portion of the loop, the one or more sets of holes being distributed along a longitudinal direction of the tubing; and a sterile absorbent covering encompassing the one or more sets of the plurality of holes, the covering being permeable to bodily fluids; attaching at the second open end of the tubing to a vacuum system; positioning the absorbent covering proximate to a surgical site; and engaging the vacuum system to a negative pressure in the tubing, causing any fluids in the absorbent covering to be automatically evacuated into the one or more sets of the plurality of holes of the tubing into the vacuum system.

These and various other aspects of the present disclosure are presented below.

DETAILED DESCRIPTION

It should be noted that while the various embodiments and examples described herein are illustrated in the context of dental surgery, it is expressly understood that the exemplary embodiments are applicable to other forms of surgery, not being limited to the dental or oral areas. Therefore, the fluids removed do not have to be blood or saliva, but may be other types of bodily fluids. Moreover, it is also expressly understood that the exemplary devices and methods disclosed herein may applied to nonhuman patients, that is, for animals. Therefore, based on the following examples, one of ordinary skill may make modifications and changes to the exemplary embodiments for non-dental/oral and/or non-human surgical scenarios without departing from the spirit and scope of this disclosure.

Figure 1:
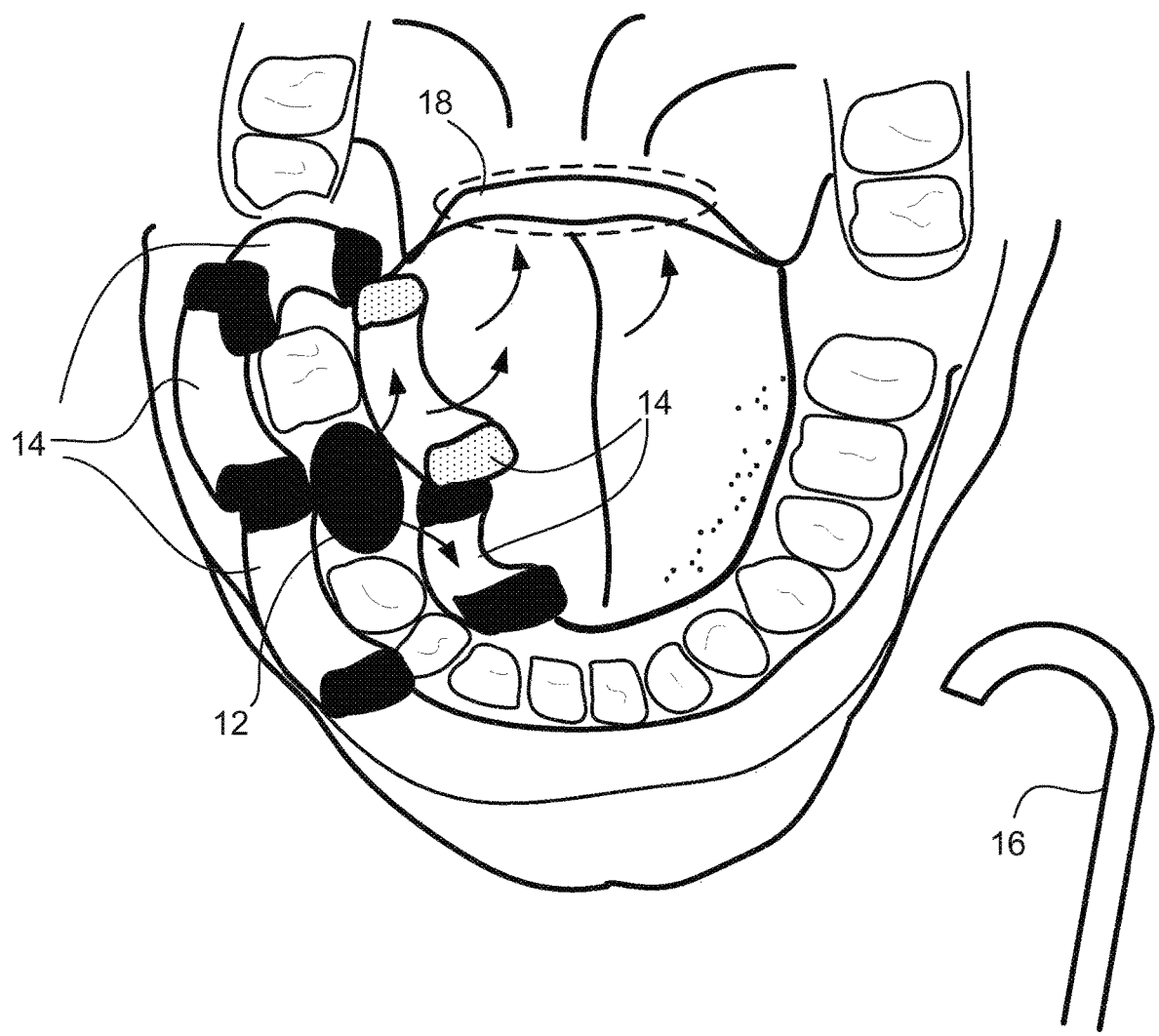
FIG. 1 is an illustration of a prior art approach to blood spillage control in an oral/dental surgical setting.

FIG. 1 is an illustration of a prior art approach 10 to blood spillage control in an oral/dental surgical setting. Specifically, the site/area 12 under surgery is surrounded by absorbent gauze 14 to control excess blood. The gauze 14 operates to absorb blood shown here as escaping (see arrows) from the surgery site/area 12. As the gauze 14 becomes saturated with blood, it no longer effectively absorbs blood and must be replaced with fresh gauze. If there are several pieces of saturated gauze about the surgery site/area 12, then the surgery must be temporarily halted while the surgeon or nurse removes, replaces and secures each individual gauze 14. Of course, this is disruptive to the surgical procedure and also very time consuming. In some cases, the act of removing/replacing the gauze 14 can traumatize the state of the surgery site/area 12, further complicating the surgery. Also, one or more gauzes 14 may become dislodged during surgery, again requiring the surgery to be temporarily halted to address the wayward gauze 14; or lost down the throat, threatening the patient's safety.

In an oral surgery scenario, a passage way 18 in the mouth is sometimes required or desired so as to allow the patient a secondary airway (the primary airway being the nasal passages). Of course, evacuating blood that has saturated the gauzes 14 will generally move (see arrows) towards the air passage 18, presenting another issue of concern for the surgeon.

It is clear that this prior art approach is at best, cumbersome and difficult to manage. What is amazing is that the above described gauze approach is the state-of-the art approach in surgical settings. For the last hundred or more years, there has not been any significant improvement practiced by surgeons.

While suction devices 16 have been introduced to supplement or aid in collecting blood/fluid during surgery, they are intrusive and are mostly utilized when there is sufficient buildup of fluid to warrant its intrusiveness. Because of their intrusiveness, the suction device 16 will have a large opening, so as to evacuate as much fluid as possible in as short a time as possible. Therefore they are intermittently used, mostly when the fluid buildup cannot be tolerated anymore by the surgeon or patient. Also, they are indiscriminant in what they collect—that is, the suction device 16 will collect whatever object that will pass through its large opening. In some instances, it can suck up unintended objects (for example, a part of loose tissue or tooth fragment) which may be catastrophic to the surgery.

Figure 2A:
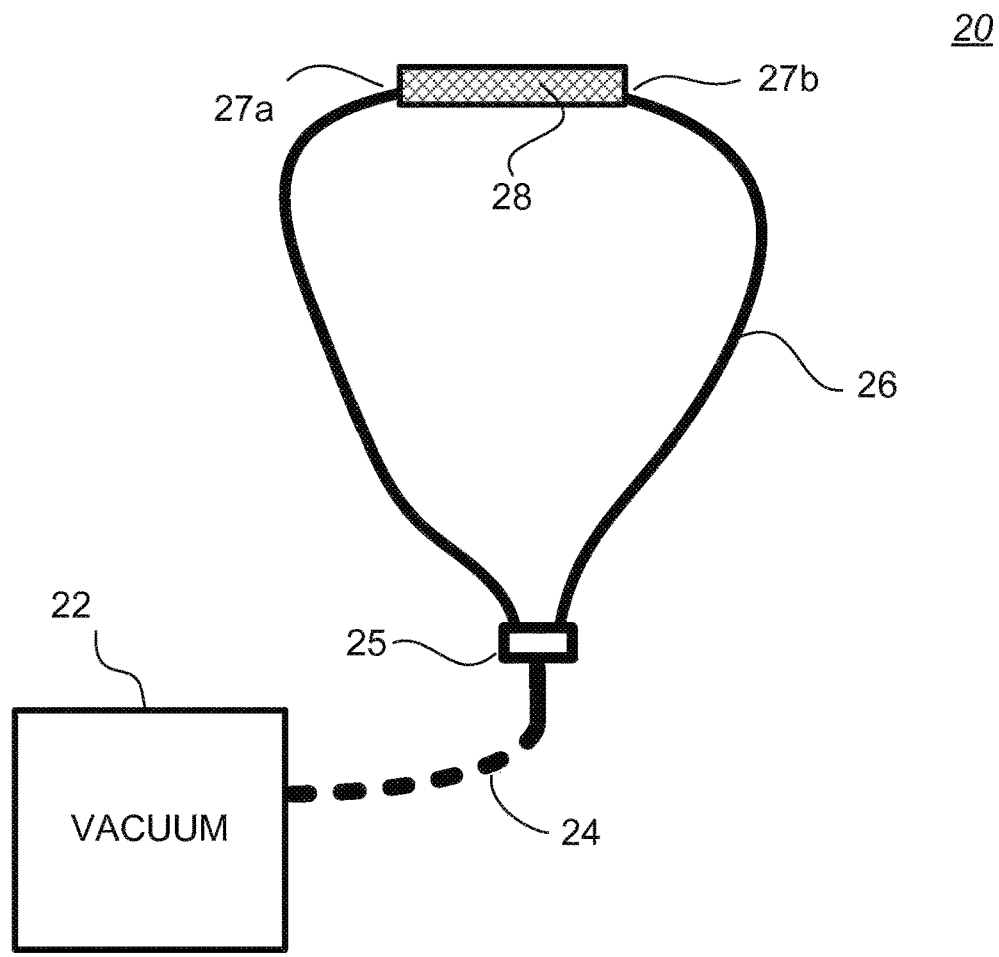
FIGS. 2A-B are illustrations of an exemplary fluid/blood collection device and a section of absorbent element.

FIG. 2A is an illustration 20 of an exemplary fluid/blood collection device 20 suitable for addressing the deficiencies of the prior art described above. The exemplary device 20 utilizes a powered vacuum system 22, which provides controllable suction through flexible tube 24 that is formed into a loop 26 with absorbent element 28 at one end and a coupler 25 at the other end, that connects to a single tube or double/multiple tube section 24. The absorbent element 28 can be placed in the vicinity of a surgical site and vacuum tube(s) 26 can draw blood through absorbent element 28 into vacuum system 22 via tubes 26, 24. The tube 26 is attached to absorbent element 28 or vice versus, whereas fluid entering absorbent element 28 is "sucked" into tube 26. To enable fluid to enter tube 26, absorbent element 28 may have porous channels that connect to tube 26 that are adjacent 27a, 27b to absorbent element 24 or tube 26 may be continuous, traveling through absorbent element 28, the tube 26 having perforations within absorbent element 28 to allow blood/fluid to enter into tube 26.

In operation, blood/fluid can be drawn into absorbing element 28 and instead of accumulating in absorbing element 28 (to become saturated,) the blood/fluid is evacuated via suction from tube 26 into tube section 24 into vacuum system 22. The combination of the vacuuming and physical "buffering" by absorbing element 28 provides a blood/fluid evacuating system that will not be saturated, thereby avoiding the need for periodic replacement. Further, pores/channels in absorbing element 28 can be small enough to avoid unintended collection/evacuation of non-fluid materials. Further, absorbing element 28, if configured of a material having large enough pores (for example, a sponge-like material), it can also provide the capability to pass air. Therefore, if absorbing element 28 is placed in front of passage way 18 (FIG. 1), an airway can be maintained while blocking fluid from entering the passage way 18.

The flexibility of tube 26 allows the exemplary device 20 to be flexibly situated about, around a surgical site, possibly conforming to natural physical contours of the anatomy of the patient. Further, absorbing element 28 may also be flexibly bendable to conform to an anatomical feature of the patient. Since the exemplary flexible tube 24 and absorbent element 28 are utilized in a surgical setting, they and the other following similar embodiments utilizing the "same" are understood to be sterile or treated to be sterile.

Figure 2B:
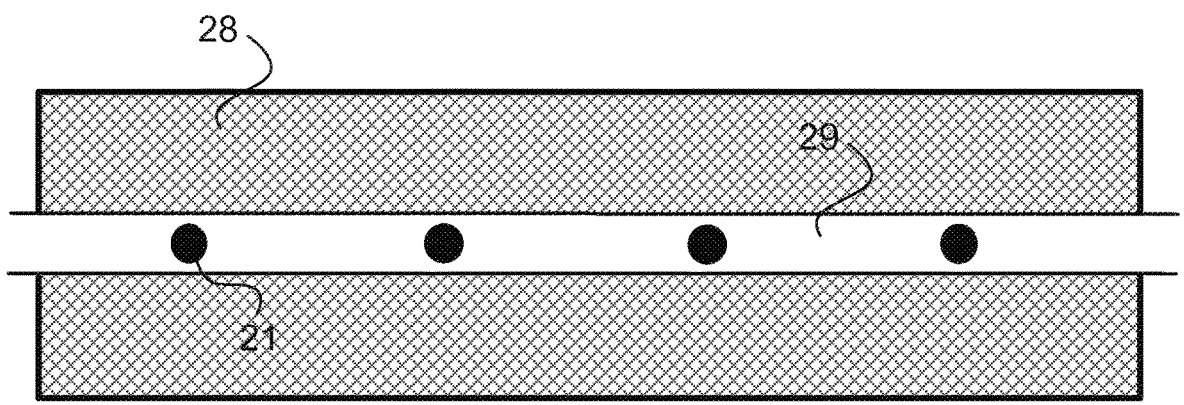

FIG. 2B is a semi-cut-away illustration of a section of absorbent element 28, showing one embodiment whereas tube section 29 inside absorbent element 28 contains a series of holes/perforations 21. The absorbent material 28 can have channels and/or pores or other features that enable fluid to be absorbed into the absorbent material 28, whereas the absorbed fluid is drawn into holes 21 via negative pressure (e.g., vacuum) from the holes 21. While only four equally spaced holes 21 are shown in this FIG., more or less holes and other positionings are contemplated. The sizes and shapes and locations of the holes 21 can also be varied, according to design preference. The tube section 29 may be of a rigid material or flexible material, again depending on design preference.

For example, in several prototypes manufactured by the inventor, the tube section 29 was from a sterile, disposable "for irrigation" use, flexible plastic tubing (commonly found in the dental industry), having a diameter of approximately 3 mm, with four radially located sets of three holes of approximately 0.1 mm in diameter, each hole spaced approximately 1 cm from each other. The absorbent element 28 was formed from a generic Polyvinyl Alcohol (PVA) sponge with a diameter of approximately 2 cm, with a lengths ranging between 2 to 5 inches, and placed over the sets of holes.

Of course, it is expressly understood that the materials and sizes used in the prototypes may be altered, changed, modified by one of ordinary skill in the art without departing from the spirit and scope of this disclosure. As one of many possible examples, the absorbent material may be made of cellulose, foam, melamine, animal, etc. or from layered fabric, and so forth. The absorbent material may vary in shape, being cylindrical, elliptical, square, etc. The absorbent material may also vary in length, being three to four inches in length, for example in a dental surgery scenario, or smaller or larger in other surgical settings.

Figure 3:
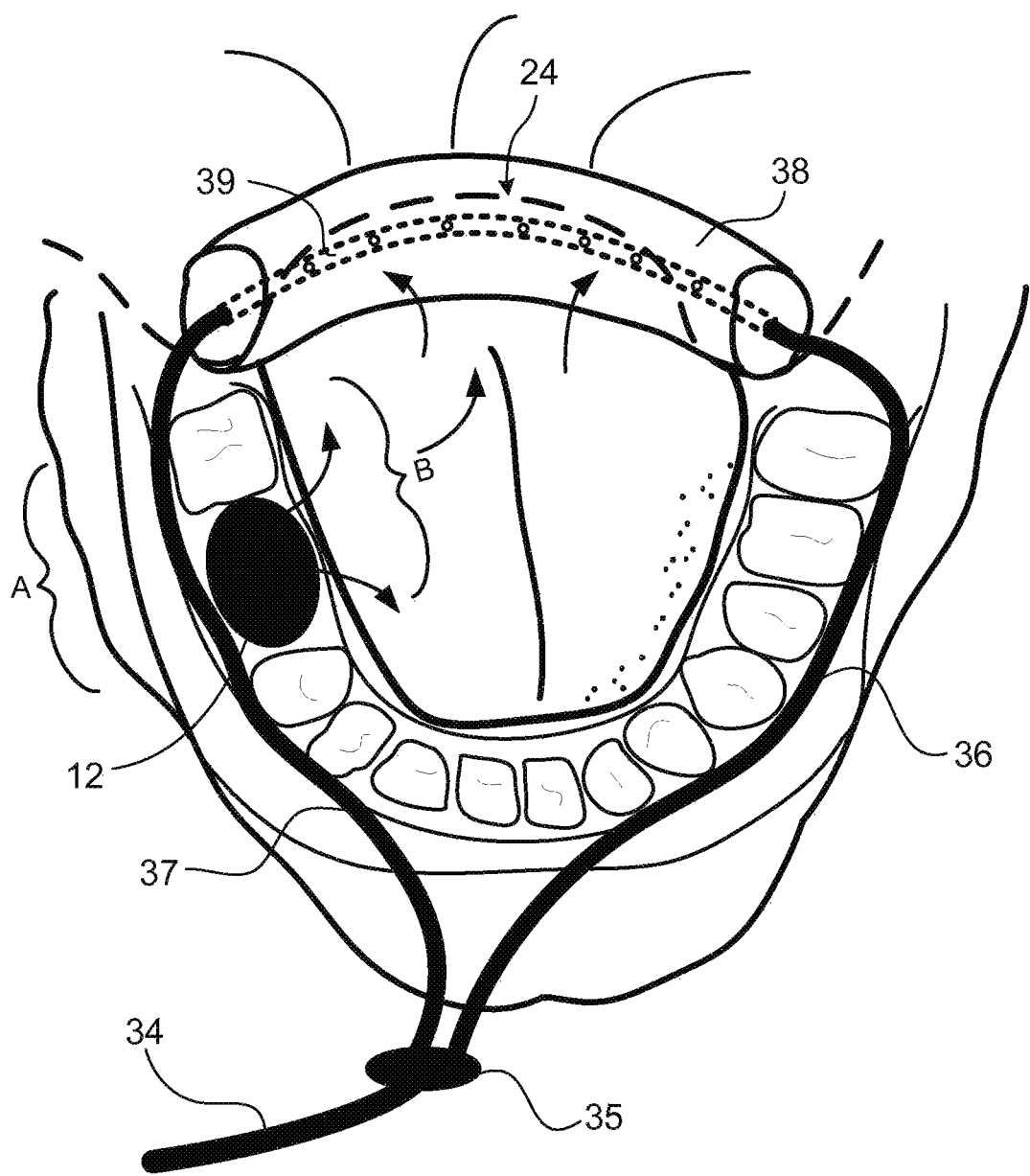
FIG. 3 is an illustration of an exemplary device in rise with an oral surgery operation.

FIG. 3 is an illustration of an exemplary device in use with an oral surgery operation. Specifically the exemplary device's absorbent element 38 is placed at the back of the mouth of the patient, and if the absorbent element 38 is of sufficient size, it can operate to "block" the throat entrance, while allowing air (if the absorbent element 38 is of a density to allow easy air passage) to enter into the passage way 18. If "interior" tube section 39 is of a flexible tube material, the absorbent element 38 can be conformed/bent to "fit" whatever anatomical feature of the patient that the surgeon desires.

Repeating the scenario detailed in FIG. 1, fluid/blood is released from the surgical site 12 which can travel towards absorbent element 38 and be evacuated from the patient/surgical area via suction arising from holes in tube section 39. The evacuated fluid/blood is carried away from absorbent element 38 through tube sections 39 to "exposed" tube 36, 37 and to tube section 34 (leading to vacuum system—not shown). The exposed tube sections 36, 37 may be joined by an optional coupler 35 which can connect to single tube section 34 or the coupler 35 may operate simply to act as a binding point for exposed tube 36, 37, so as to assist in keeping them together as they travel (together) to the vacuum system.

It should be understood tubes 39, 36, 37, 34 (and any use of the word tube presented throughout this disclosure) do not have to be circular in cross-section (e.g., be pipe-like) but may have a cross-section that is oblong, square, rectangular, triangular, of varying diameters, and so forth. Therefore, any vessel or enclosed channel that can support a vacuum and also provide a conduit for fluid can be utilized as a "tube" without departing from the spirit and scope of this disclosure. In prototypes manufactured by the inventor, tube lengths of approximately 21 inches (i.e., diameter of loop) were used with positive results.

While FIG. 3 illustrates absorbent element 38 as being placed "away" from the surgical site 12, it is understood that the exemplary device may be re-oriented to position absorbent element 38 in close proximity to the surgical site 12. For example, absorbent element 38 may be re-situated to rest along the outer section (section A) of the surgical site 12. Similarly, the absorbent element 38 may be re-situated along section B, corresponding to the inner section of the surgical site 12. The flexibility of tubes 36, 37 permit the exemplary device to be re-oriented/positioned with little effort.

It is noteworthy, that for an oral surgery or dental surgery scenario, as illustrated in this example, the location of optional coupler 35 can be such that it defines a "near mouth-sized" loop with tubes 36, 37 so that tubes 36, 37 easily fit between the patients buccal and vestibule securing the exemplary device in the patient's mouth. This is noteworthy as it reduces the probability that the exemplary device will dislodge or move during surgery.

Of course, depending on the surgery being performed, coupler 35 can be relocated to increase or decrease the size of the loop. In some embodiments, coupler 35 may be slideably moved along tube section 34, tubes 36, 37 to decrease or increase the size of the respective loop.

Figure 4A:
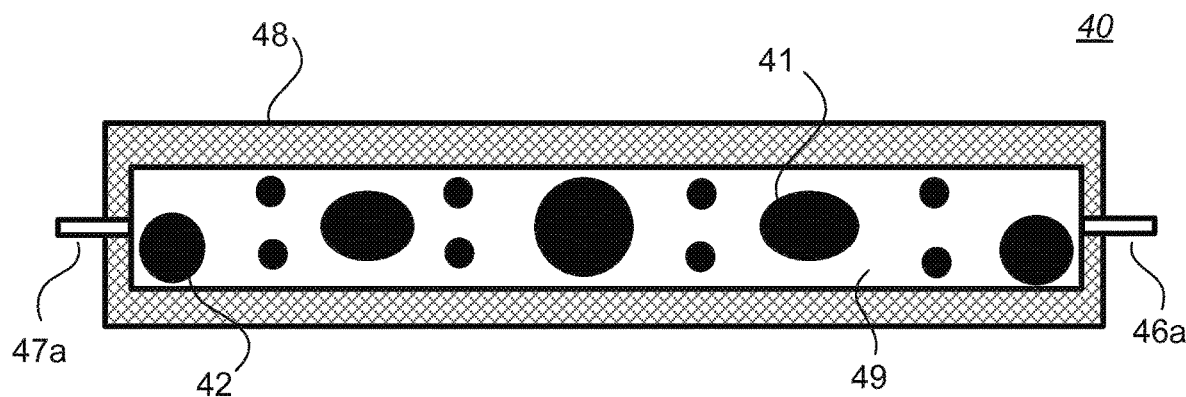
FIGS. 4A-D are (semi) cut-away illustrations of exemplary absorbent elements.

FIG. 4A is a semi-cut-away illustration of an exemplary section 40 of an exemplary absorbent element 48, showing one embodiment where tube section 49 inside absorbent element 48 is of a different diameter than external tube couplers 45a, 47a. The different sizing can facilitate the easy removal and replacement of exemplary absorbent element 48 (with tube section 49, couplers 46, 47a) from adjoining tubes (not shown). It may be convenient to have the ability to quickly "swap out" the exemplary section 40 by simply disconnecting it from the adjoining tubes.

The ability to have different sized tube section 49 and different sized holes/perforations 41, 42 along tube section 49 are also illustrated. Use of larger holes may provide higher volume fluid/blood removal characteristics along different portions of time section 49.

Figure 4B:
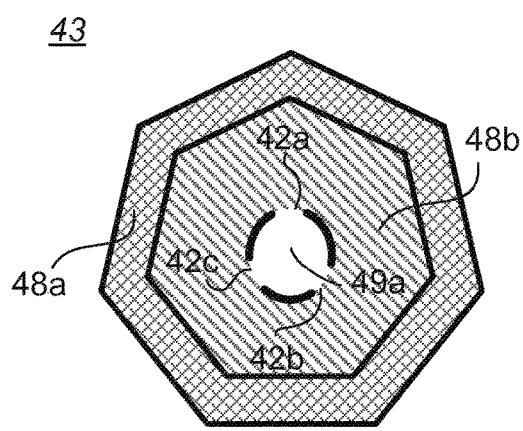

FIG. 4B is an illustration of a cross-section of another exemplary absorbent element 43, whereas different types/shapes 48a, 48b of absorbent materials are used, perhaps with different density/porosity characteristics. Tube 49a is shown with three holes 42a, 42b, 4c around the circumference of the tube 49a. Aspects of this exemplary absorbent element 43 are understood to be self-evident to one of ordinary skill in the art.

Figure 4C:
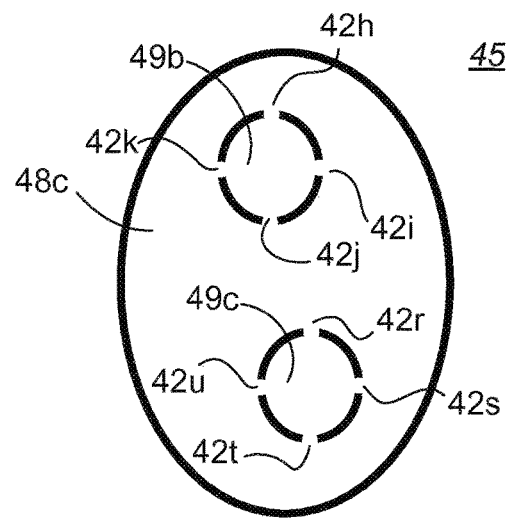

FIG. 4C is illustration of a cross-section of another exemplary absorbent element 45, whereas the shape of the absorbent element 45 is oval, having multiple tubes 49b, 49c, with respective holes 42h-k and 42r-u. This embodiment shows the use of multiple interior tubes 49b-c, the aspects of which are understood to be self-evident to one of ordinary skill in the art.

Figure 4D:
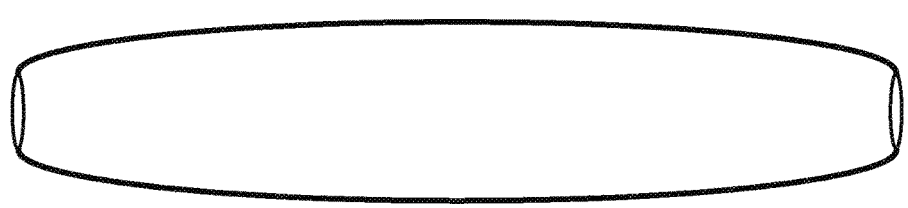

FIG. 4D is an illustration of another exemplary absorbent element 50 having a non-uniform contour, aspects of which are understood to be self-evident to one of ordinary skill in the art.

Figure 5A:
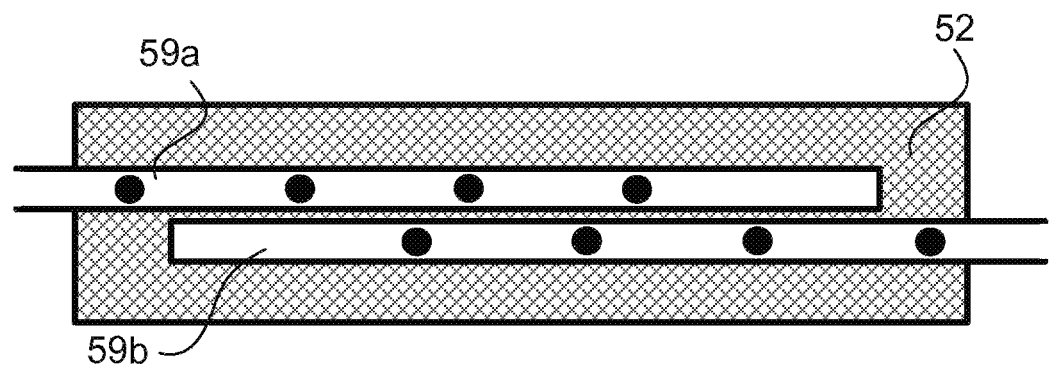
FIGS. 5A-C are (semi) cut-away illustrations of exemplary absorbent elements.

FIG. 5A is a semi-cut-away illustration of another exemplary absorbent element 52, showing truncated tubes 59a, 59b. This embodiment contemplates non-contiguous tubes 59a, 59b inside of absorbent element 52. This embodiment also contemplates the ability to possibly insert an extra tube (or remove), if needed, into absorbent element 52. That is, based on the fluid/blood evacuating needs, the surgeon can increase or decrease the effectiveness of the exemplary absorbent element 52, by inserting or removing a respective tube.

Figure 5B:
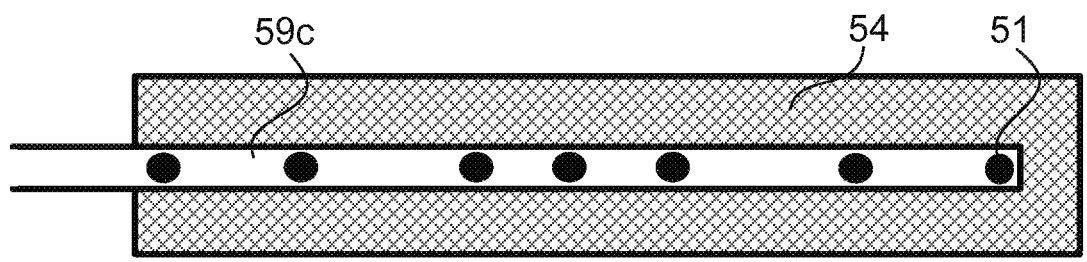

FIG. 5B is a semi-cut-away illustration of another exemplary absorbent element 54, with a one-sided tube section 59c. This embodiment contemplates a non-loop configuration where only one tube is used. This embodiment also illustrates the possibility of having different positioned holes to provide a suction profile along the exemplary absorbent element 54.

Figure 5C:
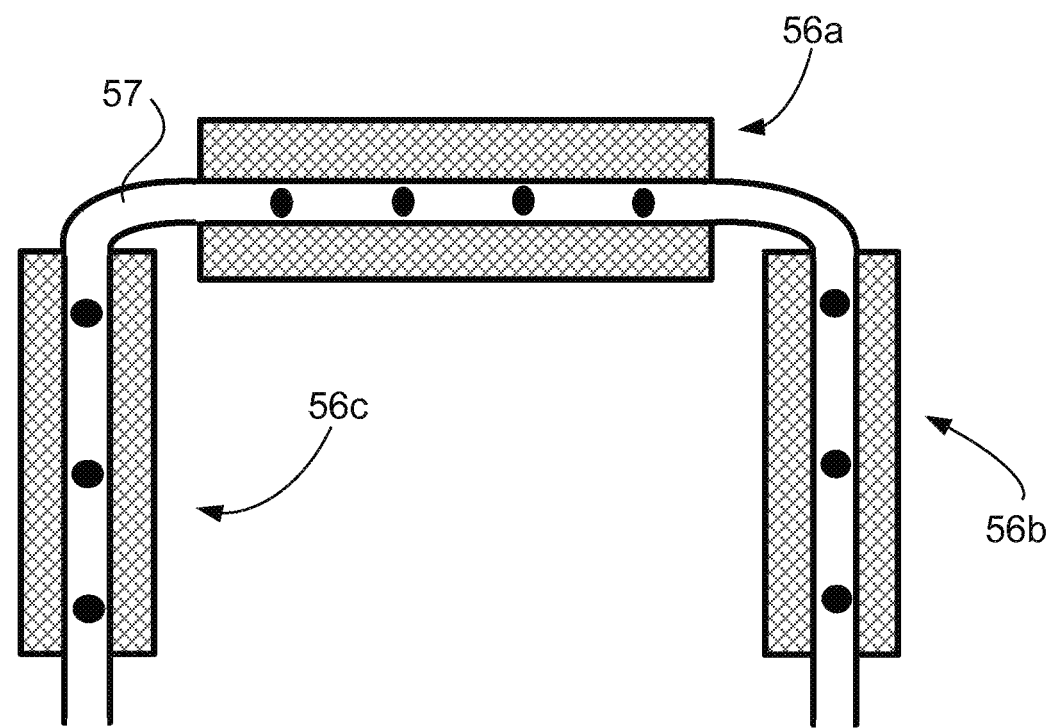

FIG. 5C is a semi-cut-away illustration of another exemplary absorbent elements 56a-c, showing a series of elements. The absorbent elements S6a-c may be rigid or flexible, whereas tube 57 may be "bendable" to conform the exemplary absorbent elements 56a-c to fit an anatomical feature of the patient (not shown).

Figure 6:
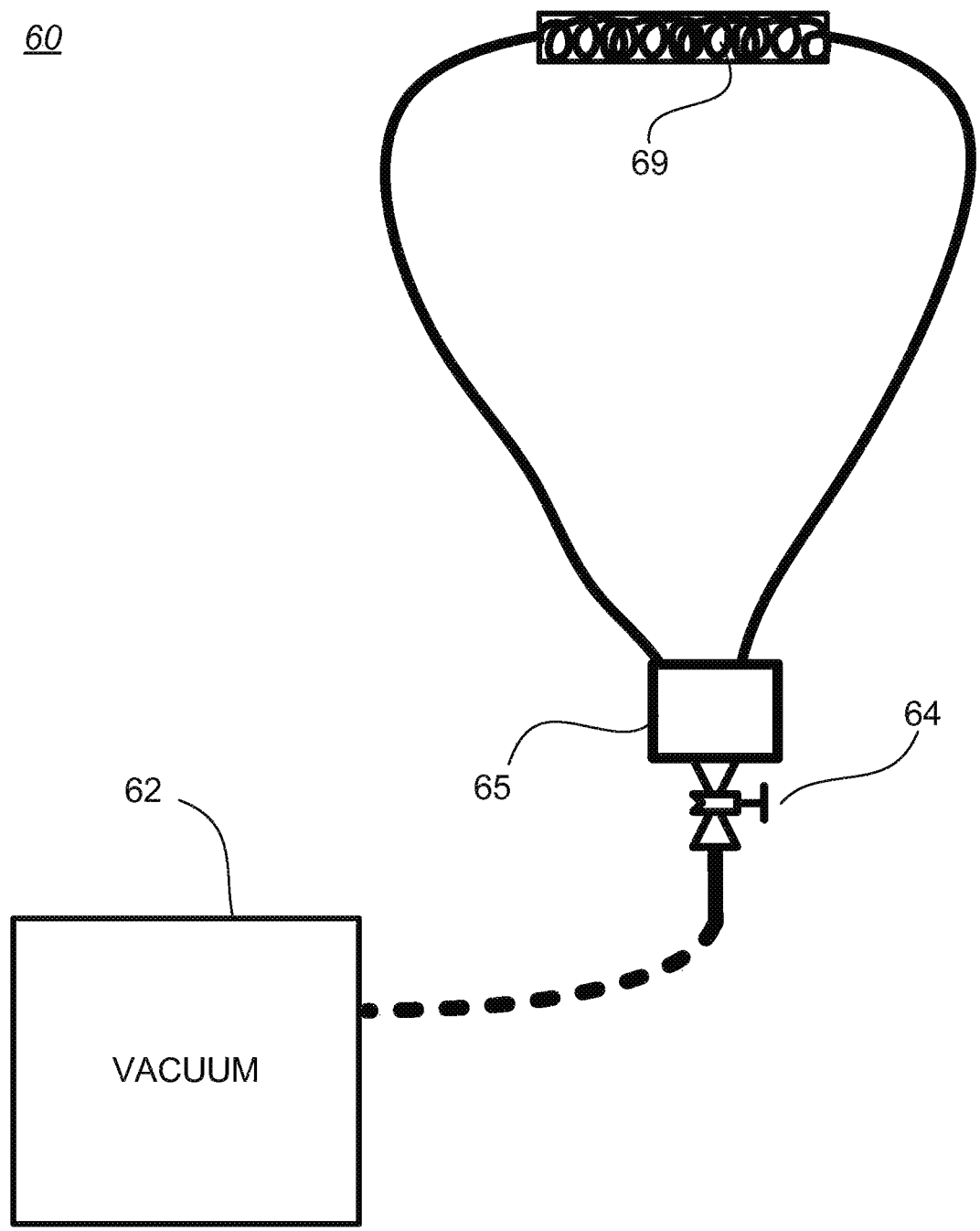
FIG. 6 is an illustration of an exemplary fluid/blood collection device with a control knob/valve.

FIG. 6 is an illustration of an exemplary fluid/blood collection device 60, whereas internal tube 69 is shown in a spiral form. Also, control of the amount of vacuum from vacuum system 62 may be facilitated by a control knob/valve 64 which may be adjacent to coupler 6S. In some embodiments, the coupler 6S may be the valve 64, or a combination thereof. The control valve 64 may directly control the vacuum system 62 or the control valve 64 may simply be a controllable external airport—allowing a measured amount of external air to be sucked into the vacuum system 62, thereby lessening the amount of suction in internal tube 69.

It will be understood that many additional changes in the details, materials, steps and arrangement of parts, which have been herein described and illustrated to explain the nature of the invention, may be made by those skilled in the art within the principle and scope of the invention as expressed in the appended claims.

What is claimed is:
1. A siphoning device configured for automatically removing fluid/blood from a surgical site, comprising:
   a sterile tubing having a first open end, a second open end, and a continuous loop disposed between the first open end and the second open end, wherein the continuous loop comprises a central portion made of a rigid material; the tubing between the first open end and the central portion of the continuous loop is flexible and the tubing between the second open end and the central portion of the continuous loop is flexible, and where the first open end and the second open end are configured to connect with a vacuum system and where the central portion of the continuous loop is configured to extend across an airway of a person's throat at a back of the person's mouth;

a coupler configured to join the first open end and the second open end;

a plurality of holes punctuating a circumference of the tubing, one or more sets of holes being distributed along a longitudinal direction of the sterile tubing;

a sterile absorbent sponge comprised of polyvinyl alcohol, the sterile absorbent sponge being at least 2 cm in diameter adapted to block the back of a person's throat and to encompass the plurality of holes, the sterile absorbent sponge being permeable to bodily fluids; and a vacuum system coupled to the first open end and the second open end of the sterile tubing, the vacuum system being configured to draw air from the sterile tubing via the first open end and the second open end causing fluids in the sterile absorbent sponge to be evacuated into the at least one or more sets of the plurality of holes of the sterile tubing and removed via the vacuum system.

2. The device of claim 1, wherein the vacuum system being configured to create a negative pressure in the tubing by removing air from the device via the first open end and the second open end, causing any fluids in the sterile absorbent sponge to be evacuated into the one or more sets of the plurality of holes of the tubing into the vacuum system.

3. The device of claim 1, wherein at least three sets of the plurality of holes are distributed along a longitudinal direction of the tubing and each set of the plurality of holes is covered by a discrete section of the sterile absorbent sponge.

4. The device of claim 1, wherein the sterile absorbent sponge is substantially cylindrical in shape and formed from at least one of a cellulose, foam, melamine, animal, and layered fabric material.

5. The device of claim 1, wherein the coupler is moveable over two sections of the tubing to allow the loop to be increased or reduced in size.

6. The device of claim 5, where the coupler is further configured to join the length of sterile tubing to a length of tubing from a vacuum system.

7. The device of claim 6, wherein the coupler further includes a control valve so as to control an amount of vacuum pressure in the tubing.

8. The device of claim 1, wherein the tubing is at least 2 mm in diameter.

* * * * *